Figure 1:
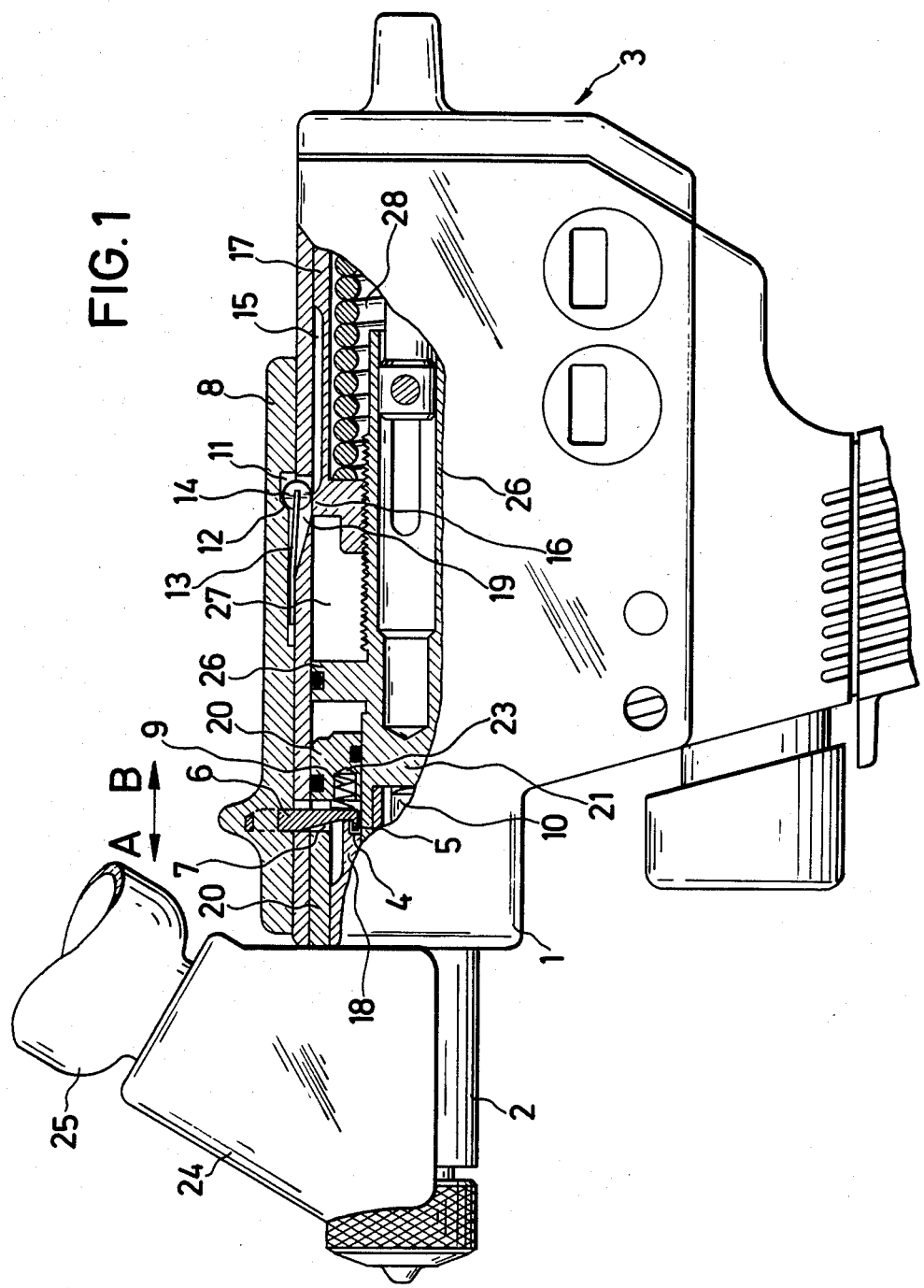

United States Patent [19]

Dettbarn et al.

[11] Patent Number: 4,642,095
[45] Date of Patent: Feb. 10, 1987

[54] LOCKING MECHANISM FOR THE REMOVABLE VACCINE PUMP OF A NEEDLELESS INJECTION INSTRUMENT

[75] Inventors: Hans-Jürgen Dettbarn, Marburg; Josef Zimmermann, Sulzbach, both of Fed. Rep. of Germany

[73] Assignee: Hoechst Aktiengesellschaft, Frankfurt, Fed. Rep. of Germany

[21] Appl. No.: 757,746

[22] Filed: Jul. 22, 1985

[30] Foreign Application Priority Data

Jul. 24, 1984 [DE] Fed. Rep. of Germany ....... 3427189

[51] Int. Cl.$^4$ ............................................... A61M 5/30
[52] U.S. Cl. ........................................ 604/72; 604/68
[58] Field of Search ................... 604/68, 72, 71, 70, 604/131, 140, 148–150, 181

[56] References Cited

U.S. PATENT DOCUMENTS

| | | | |
|---|---|---|---|
| 4,400,171 | 8/1983 | Dettbarn et al. | 604/68 |
| 4,411,650 | 10/1983 | Dettbarn et al. | 604/72 |
| 4,560,377 | 12/1985 | Geat et al. | 604/71 |

FOREIGN PATENT DOCUMENTS 1084442 6/1960 Fed. Rep. of Germany ........ 604/68

Primary Examiner—C. Fred Rosenbaum
Assistant Examiner—Gene B. Kartchner
Attorney, Agent, or Firm—Finnegan, Henderson, Farabow, Garrett & Dunner

[57] ABSTRACT

In a needleless injection instrument with a removable vaccine pump, the motor housing (1) is provided with a receiving bush (20) which is to receive the vaccine pump. In an opening (7) in the motor housing (1) and the receiving bush (20), a bolt (6) is located which is loaded by a spring (9) and has a nose (5) which engages in a recess (4) in the pump housing (18). The motor housing is also provided with a displaceable operating element (8), to which the bolt (6) is connected and which has a recess (11) for receiving a locking device (14). The locking device (14) is fixed by means of a leaf spring (13) to the motor housing; it can engage either in a groove (15), located in a spring housing (17) provided in the motor housing, or in the recess (11) of the operating element (8).

2 Claims, 2 Drawing Figures

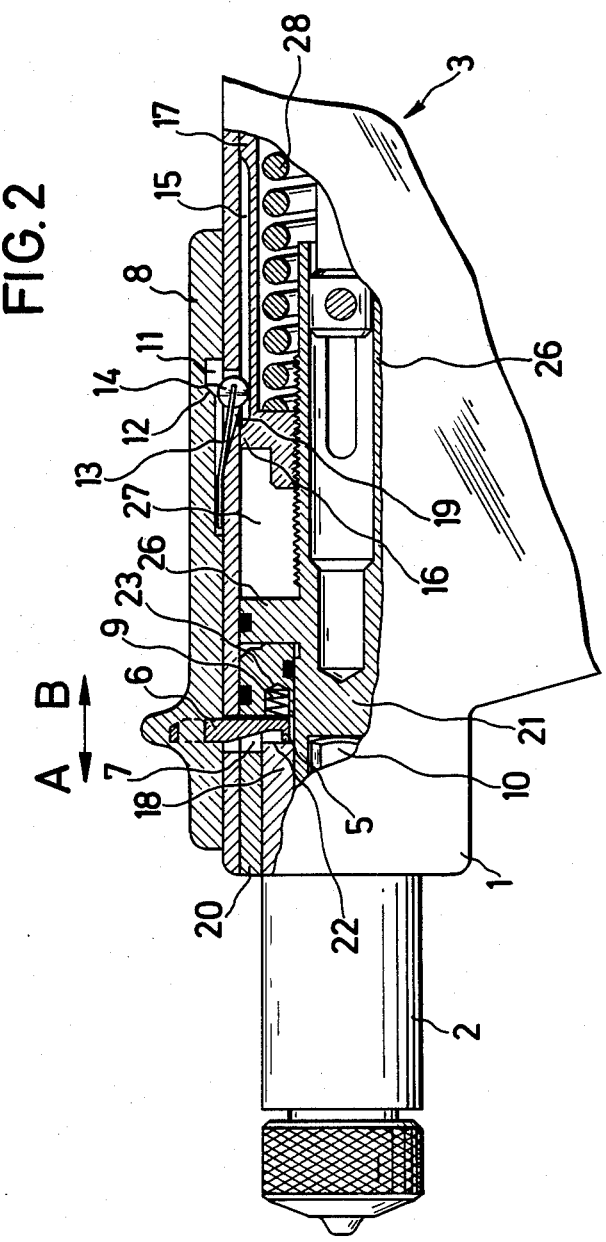

LOCKING MECHANISM FOR THE REMOVABLE VACCINE PUMP OF A NEEDLELESS INJECTION INSTRUMENT

The invention relates to a locking mechanism for the removable vaccine pump of a needleless injection instrument with a spring-driven motor for the vaccine pump, the working piston of the motor together with the spring housing being displaceably arranged in the cylindrical bore of the motor housing and having a piston shaft, the motor housing being provided with a receiving bush which is to receive the vaccine pump and the pump housing of the vaccine pump being releasably joined to the motor housing and the pump ram of the vaccine pump being releasably joined to the piston shaft.

Injection instruments of the said type have been disclosed by U.S. Pat. Nos. 4,400,172 and 4,400,171.

The disadvantage is that the vaccine pump can be turned and/or removed while the working piston of the drive motor is tensioned, i.e. in the charged state of the injection instrument.

The invention is intended to provide a remedy for this disadvantage. The invention, as defined in the patent claim, achieves the object in such a way that (a) in an opening in the motor housing and the receiving bush, a bolt is located which is loaded by a spring and has a nose which engages in a corresponding recess in the pump housing, (b) the motor housing is provided with a displaceable operating element, to which the bolt is connected and which has a recess for receiving a locking device, and (c) the locking device is fixed by means of a leaf spring to the motor housing and can engage either in a groove provided in the spring housing or in a recess of the operating element.

The motor housing can be provided with a dovetail guide for receiving the operating element.

The invention is explained below in more detail by reference to drawings which illustrate only one possible embodiment and in which:

FIG. 1 shows a side view of the injection instrument, partially in section, in the loaded state and locked, and FIG. 2 shows a detail of the side view of the injection instrument according to FIG. 1 in the unloaded state and unlocked.

The needleless injection instrument essentially comprises a vaccine pump 2 for the medium to be injected, which pump is releasably connected to a drive motor 3. The vaccine pump 2 carries the fitting 24 for the vaccine container 25. The working piston 26 of the drive motor 3 is arranged in a cylindrical bore 27 of the motor housing 1, as is the receiving bush 20 for the vaccine pump 2. The working piston 26 has a spring housing 17 in which the drive spring 28 for the working piston 26 is located. The pump housing 18 is releasably joined to the motor housing 1 via the receiving bush 20 and the pump ram 10 is releasably joined to the piston shaft 21 of the working piston 26. The motor housing 1 and the receiving bush 20 have an opening 7 in which a bolt 6 is arranged. The bolt 6 is loaded in the direction A by a spring 9 which is located in a bore 23 in the receiving bush 20. The bolt 6 has a nose 5 which can engage in a corresponding recess 4 in the pump housing 18. The motor housing 1 is provided with an operating element 8 which is displaceable in the direction of the arrows A and B and to which the bolt 6 is connected. The operating element 8, which can be guided in a dovetail guide (not shown), has a recess 11 with a ramp 12 for receiving a locking device 14. The locking device 14 is fixed by means of a leaf spring 13 to the motor housing 1 which is provided at this point with a perforation 19, so that the locking device 14 can engage either in a recess 11 of the operating element 8 or in a groove 15 provided in the spring housing 17.

With the injection instrument tensioned (FIG. 1), the raise 16 of the spring housing 17 comes to lie underneath the locking device 14, for example a roll or a ball. As a result, the locking device 14 is retained in the recess 11, so that a displacement of the operating element 8 relative to the motor housing 1 is impossible. The vaccine pump 2 can be neither turned nor uncoupled (locked state).

With the injection instrument untensioned (FIG. 2), the groove 15 of the spring housing 17 comes to lie underneath the locking device 14. When the operating element 8 is pushed back in the direction of the arrow B, the ramp 12 forces the locking device 14 into the groove 15 of the spring housing 17. The operating element 8 can be moved to and fro, and the vaccine pump can be turned and uncoupled (unlocked state).

On couplings, the vaccine pump 2 is turned about its longitudinal axis by 90° relative to the normal position and pushed into the receiving bush 20 of the drive motor 3. As a result, the plane rear face 22 of the pump housing 18 bears against the nose 5 of the bolt 6 and pushes the bolt and the operating element 8 fixed thereto in the direction of the arrow B against the force of the spring 9. The vaccine pump 2 is then turned into its normal position, so that the nose 5 can engage in the recess 4 in the pump housing 18. On engagement, the operating element 8 and the bolt 6 are pushed by the spring 9 in the direction of the arrow A. Uncoupling of the vaccine pump 2 is possible, as already stated, only in the unloaded state of the injection instrument, that is to say in the released state of the spring 28. In this instance, the operating element 8 and the bolt 6 fixed thereto is pushed by hand against the force of the spring 9 in the direction of the arrow B and held in this position. The nose 5 of the bolt 6 releases the vaccine pump 2 which can then be turned by 90° relative to its normal position and withdrawn from the receiving bush 20.

We claim:

1. A locking mechanism for locking a removable vaccine pump in a needleless injection instrument with a spring-driven drive motor, said needleless injection instrument of the type including a motor housing having a cylindrical bore, a working piston having a groove and being disposed in said cylindrical bore and arranged to be displaceable between a tensioned and an untensioned position, a receiving bushing for receiving said removable vaccine pump, said bushing being disposed in said cylindrical bore, and a piston shaft attached to said working piston and displaceable in said bushing, said vaccine pump of the type including a pump housing and being releasably attached to said bushing, and a pump ram releasably attached to said piston shaft, said locking mechanism comprising:

an operating element having a recess and being displaceably connected to said motor housing;

first and second aligned openings formed in said motor housing and said bushing, respectively;

a recess formed in said pump housing and aligned with said first and second openings;

a bolt fixedly attached to said operating element and disposed in said first and second openings, said bolt being engageable with said pump housing recess for locking said pump housing to said motor housing;

spring means for biasing said bolt toward engaging said pump housing recess;

a locking device engageable with said operating element recess for locking said bolt in engagement with said pump housing recess when said working piston is in said tensioned position; and a leaf spring fixing said locking device to said motor housing and biasing said locking device into said groove in said working piston when said working piston is in said untensioned position.

2. A locking mechanism according to claim 1, wherein said motor housing further comprises a dovetail guide for displaceably receiving said operating element.

* * * * *